US006846631B2

(12) United States Patent
Beck et al.

(10) Patent No.: US 6,846,631 B2
(45) Date of Patent: Jan. 25, 2005

(54) DETECTION OF *FUSARIUM* SPECIES INFECTING CORN USING THE POLYMERASE CHAIN REACTION

(75) Inventors: James Joseph Beck, Morrisville, NC (US); Charles Jason Barnett, Carrboro, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/961,755

(22) Filed: Sep. 24, 2001

(65) Prior Publication Data

US 2003/0113722 A1 Jun. 19, 2003

(51) Int. Cl.[7] .......................... C12Q 1/68; C12P 19/34; C07H 21/04

(52) U.S. Cl. ........................ 435/6; 435/91.2; 435/91.1; 536/24.3

(58) Field of Search ......................... 435/6, 91.2, 91.1; 536/24.3

(56) References Cited

U.S. PATENT DOCUMENTS

| | | | | |
|---|---|---|---|---|
| 4,683,195 A | | 7/1987 | Mullis et al. | 435/6 |
| 4,683,202 A | | 7/1987 | Mullis | 435/91 |
| 5,585,238 A | | 12/1996 | Ligon et al. | 435/6 |
| 5,792,611 A | * | 8/1998 | Hamelin | 435/6 |
| 5,800,997 A | | 9/1998 | Beck | 435/6 |
| 5,827,695 A | | 10/1998 | Beck | 435/91.2 |
| 5,955,274 A | | 9/1999 | Ligon et al. | 435/6 |

OTHER PUBLICATIONS

Li et al. Phytopathology, 2000, vol. 90(5). p. 491–497.*
Search Report, Accession No. U.61606.*
GenBank Accession No. U34497 [online], [retrieved on Nov. 2, 2001]. Retrieved from the Internet: <URL: http://www.ncbi.nlm.nih.gov>, first published Jan. 31, 1997.
GenBank Accession No. U34500 [online], [retrieved on Nov. 2, 2001]. Retrieved from the Internet: <URL: http://www.ncbi.nlm.nih.gov>, first published Jan. 31, 1997.
GenBank Accession No. U34501 [online], [retrieved on Nov. 2, 2001]. Retrieved from the Internet: <URL: http://www.ncbi.nlm.nih.gov>, first published Jan. 31, 1997.
GenBank Accession No. U34520 [online], [retrieved on Nov. 2, 2001]. Retrieved from the Internet: <URL: http://www.ncbi.nlm.nih.gov>, first published Jan. 31, 1997.
GenBank Accession No. U34555 [online], [retrieved on Nov. 2, 2001]. Retrieved from the Internet: <URL: http://www.ncbi.nlm.nih.gov>, first published Jan. 31, 1997.
GenBank Accession No. U34558 [online], [retrieved on Nov. 2, 2001]. Retrieved from the Internet: <URL: http://www.ncbi.nlm.nih.gov>, first published Jan. 31, 1997.
GenBank Accession No. U34559 [online], [retrieved on Nov. 2, 2001]. Retrieved from the Internet: <URL: http://www.ncbi.nlm.nih.gov>, first published Jan. 31, 1997.
GenBank Accession No. U34578 [online], [retrieved on Nov. 2, 2001]. Retrieved from the Internet: <URL: http://www.ncbi.nlm.nih.gov>, first published Jan. 31, 1997.
Desjardins, A.E. and Plattner, R.D. *Distribution of Fumonisins in Maize Ears Infected with Strains of Fusarium moniliforme that Differ in Fumonisin Production Plant Disease*, vol. 82, No. 8 (Aug. 1998), pp. 953–958.
Doohan, et al. *The use of species–specific PCR–based assays to analyse Fusarium ear blight of wheat Plant Pathology*, vol. 47 (1998), pp. 197–205.
Johanson, A. and Jeger M. *Use of PCR for detection of Mycosphaerella fijiensis and M. musicola, the causal agents of Sigatoka leaf spots in banana and plantain Mycological Research*, vol. 97, No. 6 (1993), pp. 670–674.
Lee, et al. *A rapid, high yield mini–prep method for isolation of total genomic DNA from fungi Fungal Genetics Newsletter*, No. 35 (Jun., 1988), pp. 23–24.
Lee, S.B. and Taylor, J.W., "Isolation of DNA from fungal mycelia and single spores." In: eds. Innis, et al., *PCR Protocols: A Guide to Methods andApplications* (New York, Academic Press, Inc., 1990) pp. 282–287.
Munkvold, G.P. and Desjardins, A.E., *Fumonisins in Maize: Can we Reduce Their Occurrence? Plant Disease*, 1997. vol. 81, No. 6, pp. 556–565.
Nazar, et al. *Potential use of PCR–amplified ribosomal intergenic sequences in the detection and differentiation of verticillium wilt pathogens Physiological and Molecular Plant Pathology*, vol. 39, (1991), pp. 1–11.
Nicholson, et al., *Detection and quantification of Fusarium culmorum and Fusarium graminearum in cereals using PCR assays Physiological and Molecular Plant Pathology*, vol. 53, Article No. pp980170 (1998), pp. 17–37.
O'Donnell, et al., *Gene genealogies reveal global phylogeographic structure and reproductive isolation among lineages of Fusarium graminearum, the fungus causing wheat scab Proceedings of the National Academy of Sciences*, vol. 97, No. 14 (Jul. 5, 2000), pp. 7905–7910.
O'Donnell, et al., *Molecular systematics and phylogeography of the Gibberella fujikuroi species complex Mycologia*, vol. 90, No. 3, (1998), pp. 465–493.
Raeder, U. and Broda, P. *Rapid preparation of DNA from filamentous fungi Letters in Applied Microbiology*, vol. 1 (1985), pp. 17–20.
Schesser, K., et al. *Use of Polymerase Chain Reaction to Detect the Take–All fungus, Gaeumannomyces graminis, in Infected Wheat Plants Applied and Environmental Microbiology*, vol. 57, No. 2 (1990), pp. 553–556.
White, et al. "Amplification and direct sequencing of fungal ribosomal RNA genes for phylogenetics." In: eds. Innis, et al., *PCR Protocols: A Guide to Methods and Applications* (New York, Academic Press, Inc., 1990) pp. 315–322.

* cited by examiner

*Primary Examiner*—Ethan Whisenant
*Assistant Examiner*—J. Tung
(74) *Attorney, Agent, or Firm*—Mary Kakefuda

(57) ABSTRACT

The present invention relates to the use of primers in polymerase chain reaction assays for the detection of a *Fusarium proliferatum*, *F. verticillioides* and *F. subglutinans*. Specific primers are identified as being useful for the identification of fungal isolates using PCR based techniques.

2 Claims, No Drawings

DETECTION OF *FUSARIUM* SPECIES INFECTING CORN USING THE POLYMERASE CHAIN REACTION

FIELD OF THE INVENTION

The present invention relates to the use of primers in polymerase chain reaction assays for the detection of maize *Fusarium* ear rot pathogens *Fusarium subglutinans, F. proliferatum*, and *F. verticillioides* (syn. *F. moniliforme*). The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack; however, despite $1 billion worth of expenditure on fungicides, worldwide crop losses amounted to approximately 10% of crop value in 1981 (James, 1981, *Seed Sci. & Technol.* 9: 679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983, *Cereal Diseases*, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981, *Proc.* 1981 *Brit. Crop Prot. Conf.*) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and *Mycosphaerella fijiensis* to triazoles to mention just a few (Jones and Clifford, *Cereal Diseases*, John Wiley, 1983).

Maize *Fusarium* ear rots are caused by *Fusarium verticillioides, F. proliferatum*, and *F. subglutinans*. The importance of the disease is derived from the production of the mycotoxin fumonisin by the causal organisms (*Compendium of Corn Diseases,* $3^{rd}$ ed., D. White Ed., APS Press, 1999). Contaminated grain can cause serious problems for the maize feed and food industries (Munkvold and Desjardins, 1997, *Plant Disease* 81(6):556–565). Fumonisins inhibit the biosynthesis of sphingolipids, changing the sphingolipid composition of a number of target tissues, and can cause a variety of diseases in animals that eat contaminated feeds (Munkvold and Desjardins, 1997). Consumption of maize contaminated with high levels of fumonisins has been epidemiologically associated with high levels of esophageal cancer in human populations in parts of the world where maize is a staple food (Munkvold and Desjardins, 1997). This situation is further complicated by the common occurrence of fumonisins in symptomless infected kernels (Desjardins and Plattner,1998, *Plant Disease* 82(8): 953–958). Though Fusarium ear rots typically do not significantly affect yield, they do introduce mycotoxins to the grain, leading to the loss of grain and seed quality.

In view of the above, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

SUMMARY OF THE INVENTION

The present invention is drawn to methods of identification of different pathotypes of plant pathogenic fungi. The invention provides primers derived from either the mitochondrial Small Subunit Ribosomal DNA sequences or Internal Transcribed Spacer (ITS) sequences of the nuclear ribosomal RNA gene (rDNA) of different fungal pathotypes.

These primers generate unique fragments in PCR reactions in which the DNA template is provided by specific fungal pathotypes and can thus be used to identify the presence or absence of specific pathotypes in host plant material before the onset of disease symptoms.

In a preferred embodiment, the invention provides diagnostic primers from Mitochondrial Small Subunit (SSU) rDNA or the Internal Transcribed Spacer (ITS) sequences of the nuclear ribosomal RNA gene for the detection of *Fusarium subglutinans, F. proliferatum*, and *F. verticillioides.*

This invention provides the possibility of assessing potential damage in a specific crop variety-pathogen strain relationship and of utilizing judiciously the diverse armory of fungicides that is available. Furthermore, the invention can be used to provide detailed information on the development and spread of specific pathogen races over extended geographical areas. The invention provides a method of detection that is especially suitable for diseases with a long latent phase.

Kits useful in the practice of the invention are also provided. The kits find particular use in the identification of *Fusarium subglutinans, F. proliferatum*, and *F. verticillioides.*

BRIEF DESCRIPTION OF THE SEQUENCES IN THE SEQUENCE LISTING

SEQ ID NO: 1 *Fusarium verticillioides* (syn. *F. moniliforme*) small subunit ribosomal RNA, mitochondrial gene encoding mitochondrial RNA, partial sequence. GenBank Accession Number U34497.

SEQ ID NO: 2 *Fusarium proliferatum* NRRL 22944 small subunit ribosomal RNA, mitochondrial gene encoding mitochondrial RNA, partial sequence. GenBank Accession Number U34500.

SEQ ID NO: 3 *Gibberella zeae* (syn. *Fusarium graminearum*) small subunit ribosomal RNA, mitochondrial gene encoding mitochondrial RNA, partial sequence. GenBank Accession Number U34520.

SEQ ID NO: 4 *Fusarium subglutinans* small subunit ribosomal RNA, mitochondrial gene encoding mitochondrial RNA, partial sequence. GenBank Accession Number U34501.

SEQ ID NO: 5 *Fusarium subglutinans* internal transcribed spacer RNA. GenBank Accession Number U34559.

SEQ ID NO: 6 *Gibberella zeae* NRRL 5883 internal transcribed spacer RNA. GenBank Accession Number U34578.

SEQ ID NO: 7 *Fusarium proliferatum* NRRL 22944 internal transcribed spacer RNA. GenBank Accession Number U34558.

SEQ ID NO: 8 *Fusarium verticillioides* (syn. *F. moniliforme*) internal transcribed spacer RNA. GenBank Accession Number U34555.

SEQ ID NO: 9 Oligonucleotide Primer ITS1

SEQ ID NO: 10 Oligonucleotide Primer ITS2

SEQ ID NO: 11 Oligonucleotide Primer ITS3

SEQ ID NO: 12 Oligonucleotide Primer ITS4

SEQ ID NO: 13 Oligonucleotide Primer FCORN1

SEQ ID NO: 14 Oligonucleotide Primer FCORN2

SEQ ID NO: 15 Oligonucleotide Primer FSUB1

SEQ ID NO: 16 Oligonucleotide Primer FSUB2

SEQ ID NO: 17 Oligonucleotide Primer FSUB3

SEQ ID NO: 18 Oligonucleotide Primer FVERT1

SEQ ID NO: 19 Oligonucleotide Primer FVERT2

SEQ ID NO: 20 Oligonucleotide Primer FPRO1

SEQ ID NO: 21 Oligonucleotide Primer FPRO2

SEQ ID NO: 22 Oligonucleotide Primer FPRO3

SEQ ID NO: 23 Oligonucleotide Primer MS1

SEQ ID NO: 24 Oligonucleotide Primer MS2

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include primers derived from partial sequences of the mitochondrial small subunit ribosomal RNA genes (SSU rDNA) or the Internal Transcribed Spacer (ITS) sequences of the nuclear ribosomal RNA gene regions of particular fungal pathogens that are capable of identifying the particular pathogen.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991, *Applied and Environ. Microbiol.* 57: 553–556), and random amplified polymorphic DNA (i.e. RAPD) markers were able to distinguish numerous races of *Gremmeniella abietina*, the causal agent of scleroderris canker in conifers. U.S. Pat. No. 5,585,238 (herein incorporated by reference in its entirety) describes primers derived from the ITS sequences of the ribosomal RNA gene region of strains of Septoria, Pseudocercosporella, and *Mycosphaerella* and their use in the identification of these fungal isolates using PCR-based techniques. In addition, U.S. Pat. No. 5,955,274 (herein incorporated by reference in its entirety) describes primers derived from the ITS sequences of the ribosomal RNA gene region of strains of Fusarium and their use in the identification of these fungal isolates using PCR-based techniques. Furthermore, U.S. Pat. No. 5,800,997 (herein incorporated by reference in its entirety) describes primers derived from the ITS sequences of the ribosomal RNA gene region of strains of Cercospora, Helminthosporium, Kabatiella, and Puccinia and their use in the identification of these fungal isolates using PCR-based techniques.

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990, in *PCR Protocols*, Innes et al., Eds., pages 315–322). In addition, the transcriptional units are separated by non-transcribed spacer sequences (NTSs). ITS and NTS sequences are particularly suitable for the detection of specific pathotypes of different fungal pathogens.

Mitochondrial small subunit rDNA sequences similarly evolve more quickly than nuclear small subunit rDNA sequences and are thus more useful in differentiating more closely related species. As with the more quickly evolving ITS region sequences the mitochondrial small subunit rDNA sequences are composed of regions of higher and lesser variability which allow the use of conserved primers such as MS1 and MS2 described by White et al. (1990, in *PCR Protocols*, Innes et al., Eds., pages 315–322) to amplify out regions that contain more variability.

The DNA sequences of the invention are from partial sequences of the mitochondrial small subunit ribosomal RNA genes (SSU rDNA) or the Internal Transcribed Spacer sequences of the ribosomal RNA gene region of different plant pathogens. The mitrochondrial SSU rDNA and nuclear ITS region DNA sequences from different pathotypes within a pathogen species or genus vary among the different members of the species or genus. Once the sequences of either of these regions has been determined for a given pathogen, these sequences can be aligned with other respective sequences from the same region for other pathogens. In this manner, primers can be derived from the mitrochondrial SSU rDNA or nuclear ITS region sequences that are specific for a given pathogen. That is, primers can be designed based on regions within either the mitrochondrial SSU or nuclear ITS region sequences that contain the greatest differences in sequence among the fungal pathotypes when similar regions are compared. These sequences and primers based on these sequences can be used to identify specific pathogens.

The present invention provides oligonucleotide primers for use in amplification-based detection of a fungal Internal Transcribed Spacer DNA sequence, wherein said primer has sequence identity with at least 10 contiguous nucleotides of the Internal Transcribed Spacer sequence from *Fusarium* spp., such as but not limited to *F. subglutinans, F. proliferatum*, or *F. verticillioides*. In a preferred embodiment, the fungal specis is *Fusarium proliferatum*. In other preferred embodiments, the ITS comprises the nucleotides sequence of SEQ ID NO: 5, 6, 7 or 8, more preferably, SEQ ID NO: 7.

In preferred embodiments, oligonucleotide primers derived from ITS sequences comprises or consists of a nucleotide sequence of SEQ ID NOs: 9–12, 21 or 22. The primers are useful in the PCR-based identification of *Fusarium proliferatum.*

The present invention also provides oligonucleotide primers for use in amplification-based detection of a fungal mitochondrial small subunit rDNA sequence, wherein said primer has sequence identity with at least 10 contiguous nucleotides of the mitochondrial small subunit ribosomal DNA sequence from *Fusarium* spp., in particular but not limited to, *F. subglutinans, F. verticillioides*, or *F. proliferatum*. More particularly, the mtSSU rDNA comprises the nucleotides sequence of SEQ ID NOs: 1–4.

In preferred embodiments, oligonucleotide primers derived from mitochondrial SSU rDNA comprise a nucleotide sequence of SEQ ID NOs: 13–20, 23, or 24. The primers are useful in the PCR-based identification of the *Fusarium* spp. pathogens of interest. In particular, the *Fusarium* spp. include, but are not limited to, *F. subglutinans* or *F. verticillioides* (syn. *F. moniliforme*). The present invention also provides for pairs of oligonucleotide primers. In one embodiment, a pair of oligonucleotide primers for use in the amplification-based detection of a fungal Internal Transcribed Spacer DNA sequence, wherein at least one of said primers is the oligonucleotide primer has sequence identity with at least 10 contiguous nucleotides of the Internal Transcribed Spacer sequence from *Fusarium* spp. such as but not limited to SEQ ID NO: 5, 6, 7 or 8. In another embodiment, the invention provides a pair of oligonucleotide primers, wherein at least one of said primers is the oligonucleotide primer of with at least 10 contiguous nucleotides of the Internal Transcribed Spacer sequence from a *Fusarium proliferatum*, such as but not limited to SEQ ID NO: 7.

In a preferred embodiment, the invention provides a pair of oligonucleotide primers wherein at least one primer consists of the nucleotide sequence of SEQ ID NOS: 9–12, 21 or 22. Preferred pairs of primers are: ITS1 (SEQ ID NO: 9) and FPRO2 (SEQ ID NO: 21); ITS1 (SEQ ID NO: 9) and FPRO3 (SEQ ID NO: 22); ITS3 (SEQ ID NO: 1) and FPRO2 (SEQ ID NO: 21); and ITS3 (SEQ ID NO: 11) and FPRO3 (SEQ ID NO: 22).

In another embodiment, a pair of oligonucleotide primers for use in the amplification-based detection of a fungal mitochondrial small subunit ribosomal DNA sequence, wherein at least one of said primers is the oligonucleotide primer has sequence identity with at least 10 contiguous nucleotides of the mitochondrial small subunit ribosomal DNA sequence from *Fusarium* spp., such as but not limited to SEQ ID NOS: 1–4. In another embodiment, the invention provides a pair of oligonucleotide primers, wherein at least one of said primers is the oligonucleotide primer of with at least 10 contiguous nucleotides of the mitochondrial small subunit ribosomal DNA sequence from a *Fusarium* spp., such as but not limited to SEQ ID NOS: 1–4. In particular, the *Fusarium* spp. are but are not limited to, *Fusarium subglutinans, Fusarium proliferatum* and/or *Fusarium verticillioides* (syn. *F. moniliforme*).

In a preferred embodiment, the a pair of oligonucleotide primers wherein one primer consists of a mitochondrial small subunit ribosomal DNA derived oligonucleotide primer of SEQ ID NOS: 13–20, 23, or 24.

In other more preferred embodiments, the invention provides pairs of oligonucleotide primers wherein said pair consists of SEQ ID NO: 15 and SEQ ID NO: 16; wherein said pair consists of SEQ ID NO: 13 and SEQ ID NO: 16; wherein said pair consists of SEQ ID NO: 14 and SEQ ID NO: 18; wherein said pair consists of SEQ ID NO: 14 and SEQ ID NO: 19; or wherein said pair consists of SEQ ID NO: 14 and SEQ ID NO: 20.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991, *Physiol. and Molec. Plant Pathol.* 39:1–11), which used PCR amplification to exploit differences in the ITS regions of *Verticillium albo-atrum* and *Verticillium dahliae* and therefore distinguish between the two species; and Johanson and Jeger (1993, *Mycol. Res.* 97: 670–674), who used similar techniques to distinguish the banana pathogens *Mycosphaerella fijiensis* and *Mycosphaerella musicola.*

The target DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

The published mitochondrial SSU rDNA or ITS rDNA sequences are compared within each pathogen group to locate divergences that might be useful to test in PCR to distinguish the different species and/or strains. From the identification of divergences, numerous primers are synthesized and tested in PCR-amplification. Templates used for PCR-amplification testing are firstly purified pathogen DNA, and subsequently DNA isolated from infected host plant tissue. Thus, it is possible to identify pairs of primers that are diagnostic, i.e. that identified one particular pathogen species or strain but not another species or strain of the same pathogen. Primers are also designed to regions highly conserved among the species to develop genus-specific primers as well as primers that will identify any of several fungal pathogens that cause a particular disease. For example, primers are developed to differentiate species of *Fusarium*: *F. proliferatum, F. verticillioides*, and *F. subglutinans.*

Preferred primer combinations are able to distinguish between the different species or strains in infected host tissue, i.e. host tissue that has previously been infected with a specific pathogen species or strain. This invention provides numerous primer combinations that distinguish *Fusarium proliferatum, F. verticillioides*, and *F. subglutinans*. The primers of the invention are designed based on sequence differences among either the mitochondrial SSU rDNA or the ITS rDNA regions. A minimum of one base pair difference between sequences can permit design of a discriminatory primer. Primers designed to a specific fungal DNA sequence can be used in combination with a primer made to a conserved sequence region flanking the region containing divergences to amplify species-specific PCR fragments. In general, primers should have a theoretical melting temperature between about 60 to about 70 degree ° C. to achieve good sensitivity and should be void of significant secondary structure and 3' overlaps between primer combinations. In preferred embodiments, primers are anywhere from approximately 5–30 nucleotide bases long.

In one embodiment, the present invention provides a method for the detection of a fungal pathogen, comprising the steps of:

(a) isolating DNA from a plant tissue infected with a pathogen;

(b) subjecting said DNA to polymerase chain reaction amplification using at least one primer having sequence identity with at least 10 contiguous nucleotides of an Internal Transcribed Spacer sequence of a *Fusarium* spp.; and (c) detecting said fungal pathogen by visualizing the product or products of said polymerase chain reaction amplification.

In preferred embodiments, the method detects infections with a pathogen, wherein said fungal pathogen *Fusarium subglutinans, Fusarium proliferatum* or *Fusarium verticillioides*. In another preferred embodiment, the ITS sequences have the nucleotide sequence of SEQ ID NO: 5, 6, 7, or 8.

In another preferred embodiment, the method uses at least one primer having the nucleotide sequence of SEQ ID NOS: 9–12, 20 or 21. In another embodiment, the present invention provides for a method for the detection of a fungal pathogen, comprising the steps of:

(a) isolating DNA from a plant tissue infected with a pathogen;

(b) subjecting said DNA to polymerase chain reaction amplification using at least one primer having sequence identity with at least 10 contiguous nucleotides of a mitochondrial small subunit rDNA sequence of a *Fusarium* spp.; and (c) detecting said fungal pathogen by visualizing the product or products of said polymerase chain reaction amplification.

In preferred embodiments, the method detects the fungal pathogens of *Fusarium subglutinans, Fusarium proliferatum* or *Fusarium verticillioides.*

In another preferred embodiment, the method uses at least one primer having the nucleotide sequence of SEQ ID NOS: 13–20, 23 or 24.

In more preferred embodiments, the methods uses a pairs of oligonucleotide primers wherein said pair consists of SEQ ID NO: 15 and SEQ ID NO: 16; wherein said pair consists of SEQ ID NO: 13 and SEQ ID NO: 16; wherein said pair consists of SEQ ID NO: 14 and SEQ ID NO: 18; wherein said pair consists of SEQ ID NO: 14 and SEQ ID NO: 19; or wherein said pair consists of SEQ ID NO: 14 and SEQ ID NO: 20.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in admixtures, in lyophilized form or in appropriate buffers. In one embodiment, the diagnostic kit used in detecting a fungal pathogen, comprises at least one primer of SEQ ID NOs: 9–12, 21 or 22 for ITS derived primers or SEQ ID NOs: 13–20, 23, or 24 for primers derived from mitochondrial small subunit ribosomal DNA.

In more preferred embodiments, the diagnostic kit used in detecting a fungal pathogen, comprises the pair of primers described above. More preferably, the pairs of primers are SEQ ID NO: 15 and SEQ ID NO: 16; SEQ ID NO: 13 and SEQ ID NO: 16; SEQ ID NO: 14 and SEQ ID NO: 18; SEQ ID NO: 14 and SEQ ID NO: 19; or SEQ ID NO: 14 and SEQ ID NO: 20.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the selection of suitable primer sequences, the testing of primers for selective and diagnostic efficacy, and the use of such primers for disease and fungal isolate detection. Such examples are provided by way of illustration and not by way of limitation.

Numerous references cited above are all incorporated herein in their entireties.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Fungal Isolates and Genomic Fungal DNA Extraction

See Tables 1 and 2 for listings of the fungal isolates used and their sources. Isolates used to validate the assays in the following examples were obtained from a number of academic institutions and collections (Table 1).

TABLE 1

| | Source of Test Isolates | | | |
|---|---|---|---|---|
| | Isolate | Source | Isolation | Geographic Origin |
| *Fusarium moniliforme* | M-1231 | Penn State[1] | Rice | Philippines |
| *Fusarium moniliforme* | M-1264 | Penn State[1] | Rice | Sierra Leone |
| *Fusarium moniliforme* | M-1329 | Penn State[1] | Rice | California, USA |

TABLE 1-continued

Source of Test Isolates

| | Isolate | Source | Isolation | Geographic Origin |
|---|---|---|---|---|
| *Fusarium moniliforme* | M-3120 | Penn State[1] | Maize | California, USA |
| *Fusarium moniliforme* | M-3125 | Penn State[1] | Maize | California, USA |
| *Fusarium sporotrichioides* | 3299 | NRRL[2] | | |
| *Fusarium subglutinans* | M-3693 | Penn State[1] | Maize | Iowa, USA |
| *Fusarium subglutinans* | M-3696 | Penn State[1] | Maize | Iowa, USA |
| *Fusarium moniliforme* | M-3744 | Penn State[1] | Rice | Australia |
| *Fusarium moniliforme* | M-5167 | Penn State[1] | Rice | Iran |
| *Fusarium moniliforme* | M-5587 | Penn State[1] | Date Palm | Iraq |
| *Fusarium moniliforme* | M-5605 | Penn State[1] | | Poland |
| *Fusarium proliferatum* | M-5991 | Penn State[1] | Swine Feed | Iowa, USA |
| *Fusarium moniliforme* | M-6173 | Penn State[1] | Rice | Malaysia |
| *Fusarium sambucinum-sulphureum* | R-6380 | Penn State[1] | Potato | Germany |
| *Fusarium moniliforme* | M-6471 | Penn State[1] | Maize | Kansas |
| *Fusarium moniliforme* | M-8510 | Penn State[1] | Rice | Nepal |
| *Fusarium moniliforme* | 6396 | NRRL[2] | Chicken Feed | Arkansas, USA |
| *Fusarium moniliforme* | 13563 | NRRL[2] | *Pinus taeda* | North Carolina, USA |
| *Fusarium moniliforme* | 25029 | NRRL[2] | *Nilaparvata lugens* | India |
| *Fusarium subglutinans* | 13588 | NRRL[2] | Maize | Iowa, USA |
| *Fusarium subglutinans* | 13599 | NRRL[2] | Maize | Zambia |
| *Fusarium subglutinans* | 20844 | NRRL[2] | Maize | Germany |
| *Fusarium proliferatum* | 94-041 | Iowa State[3] | Maize | Iowa |
| *Fusarium proliferatum* | 94-066 | Iowa State[3] | Maize | Iowa |
| *Fusarium proliferatum* | 94-129 | Iowa State[3] | Maize | Iowa |
| *Fusarium proliferatum* | 95-122 | Iowa State[3] | Maize | Iowa |
| *Fusarium proliferatum* | 95-135 | Iowa State[3] | Maize | Iowa |
| *Fusarium proliferatum* | 95-289 | Iowa State[3] | Maize | Iowa |
| *Fusarium culmorum* | R-5126 | Penn State[1] | | Minnesota, USA |
| *Fusarium graminearum* | R-8637 | Penn State[1] | | Settat, Morocco |
| *Microdochium nivale* | 15N1 | S.Edwards[4] | | United Kingdom |
| *M. nivale* var. *majus* | 93 | Novartis, Basel[5] | | — |
| *Fusarium poae* | T-427 | Penn State[1] | | Pennsylvannia, USA |
| *Fusarium avenaceum* | 64452 | ATCC[6] | Wheat | Poland |
| *Diplodia maydis* | 5139 | C.Naidoo[7] | | Illinois, USA |
| *Macrophomina phaseolina* | MP97 | J. Mihail[8] | | Missouri, USA |
| *Aspergillus flavus* | 3557 | NRRL Collection[2] | | |
| *Kabatiella zeae* | 18594 | ATCC[6] | Maize | Wisconsin, USA |
| *Cercospora zeae-maydis* | 69281L | C.Naidoo[7] | | Illinois, USA |
| *Cercospora zeae-maydis* | 26158 | ATCC[6] | Maize | New York, USA |
| *Puccinia sorghi* | VA | | | |
| *Helminthosporium maydis* | 24772 | ATCC[6] | Maize | North Carolina, USA |
| *Helminthosporium maydis* | 11534 | ATCC[6] | Maize | Maryland, USA |
| *Helminthosporium carbonum* | 16185 | ATCC[6] | Maize | Virginia, USA |
| *Helminthosporium carbonum* | 24962 | ATCC[6] | Maize | Illinois, USA |
| *Helminthosporium turcicum* | 26306 | ATCC[6] | Maize | Illinois, USA |
| *Fusarium culmorum* | 62215 | ATCC[6] | Wheat seed | Switzerland |
| *Fusarium culmorum* | R-5106 | | | Darling Downs, Australia |

[1]Fusarium Research Center; Pennsylvania State University; University Park, PA, USA
[2]USDA Agricultural Research Service Culture Collection (NRRL); Peoria, IL, USA
[3]Dept. of Plant Pathology; Iowa State University; Ames, IA, USA
[4]Dr. Simon Edwards; Harper Adams University College; Newport, United Kingdom
[5]Novartis Crop Protection Limited; Basel, Switzerland
[6]American Type Culture Collection; Rockville, MD, USA
[7]Dr. Charmaine Naidoo, Ciba Seeds Research, Bloomington, IL, USA
[8]Dr. Jeanne Mihail, University of Missouri, Columbia, MO, USA Unknown ear rot isolates cultured from field grown maize were obtained from the Novartis Seeds research station in Stanton, Minn., USA and are described in Table 2. Fungi are grown on PDA (Potato Dextrose Agar) plates. Cultures are incubated for up to 10 days at 28° C. Mycelia are ground in liquid nitrogen, and total genomic DNA is extracted using the protocol of Lee and Taylor (1990; In: *PCR Protocols: A Guide to Methods and Applications*; Eds.: Innes et al.; pages 282–287).

TABLE 2

Geographical Source of Unknown Ear Rot Isolates

| Isolate Designation | Geographical Region | Isolate Designation | Geographical Region |
|---|---|---|---|
| Fm001 | Nebraska | Fm042 | North Carolina |
| Fm002 | Georgia | Fm043 | Colorado |

TABLE 2-continued

Geographical Source of Unknown Ear Rot Isolates

| Isolate Designation | Geographical Region | Isolate Designation | Geographical Region |
|---|---|---|---|
| Fm003 | Iowa | Fm044 | Mississippi |
| Fm004 | Ohio | Fm045 | Hawaii |
| Fm005 | Illinois | Fm046 | Hawaii |
| Fm006 | Illinois | Fm047 | Hawaii |
| Fm007 | Illinois | Fm048 | Hawaii |
| Fm008 | Illinois | Fm049 | Hawaii |
| Fm009 | Ohio | Fm050 | Hawaii |
| Fm010 | Ohio | Fm051 | Hawaii |
| Fm011 | | Fm052 | Hawaii |
| Fm012 | Ohio | Fm053 | Hawaii |
| Fm013 | Kentucky | Fm054 | Hawaii |
| Fm014 | Illinois | Fm055 | Hawaii |
| Fm034 | Kentucky | Fm056 | Hawaii |
| Fm035 | Illinois | Fsub1 | Minnesota |
| Fm036 | | Fsub2 | Minnesota |
| Fm037 | | Fsub3 | Minnesota |
| Fm039 | Hawaii | Fsub4 | Minnesota |
| Fm040 | Hawaii | BC3 189 | Minnesota |
| Fm041 | North Carolina | | |

Example 2

DNA Extraction from Maize Tissues

DNA is extracted from maize tissues by one of two methods. The method described in Example 2A is used for bulk extractions of maize leaves taken from some 10–15 plants at either the ear, the node above the ear, or the node below the ear. Example 2B describes a method used for extracting DNA from maize tissues in 1.5 mL tubes. This method may be used for concentrating the sample around one lesion or for testing anther or axil material.

Example 2A

Large-Scale DNA Extraction from Maize Leaves

DNA is extracted from maize leaves in a bulk maceration as follows:

(1) A sample consists of whole maize leaves collected from some 20 plants from the same position on the plant (ear leaf, third ear below leaf, etc.) and kept separated accordingly. The top third of each leaf is taken and extracted in bulk.

(2) The sample is placed in a Bioreba (Reinach, Switzerland) heavy duty plastic bag (cat#490100). The plant tissue is weighed, plastic bag with leaves minus the tare (weight of the plastic bag).

(3) An equal volume (ml) of CTAB Extraction Buffer (100 mM Tris, pH 8.0; 1.4 M NaCl; 20 mM $Na_2$-EDTA; 2% Hexadecyltrimethyl ammonium bromide (CTAB); 2% Polyvinylpyrolidine (PVPP); 0.1% ascorbic acid; 0.2% β-mercaptoethanol) is added per weight (g) of maize tissue. The tissue is macerated using a Bioreba Homex 6 homogenizer set at 70. The tissue is ground until fibrous.

(4) The extraction juice is homogenized and is aliquoted into eppendorf tubes on ice.

(a) The concentrated extract is boiled for 5 minutes.

(b) The boiled extract is placed on ice for two minutes. The boiled extract is then centrifuged for 5 minutes at 10,000×G.

(c) 1:40 dilutions of the supernatant from the microfuged extract in cold $dH_2O$ are made and used as sample DNA template in PCR assays.

(d) The diluted extracts are stored on ice until ready to use.

For the purpose of showing that the assays do not cross-react with maize tissue, a sample of field-grown maize visually assessed as healthy obtained from Franklin, Id., USA near the end of June 1999 is used to test for background effects. DNA preparations are made from the sample using the protocol outlined in this example (The extract is designated 1999 Maize sample #1).

Example 2B

Small-scale DNA Extraction From Anther, Axil, and Husk Tissues Collected from Field-grown Maize Samples of Maize tissues consisting of anther, axil, or husk material are received in eppendorf tubes. Sample sizes are limited to occupying ⅕ volume of the 1.5 mL tube:

(1) Check/set the temperature of the dry bath is at 90° C. Transport samples on Dry-ice to Sawz-all. Keep samples on Dry-ice or at minus 80° C. before and after grinding.

(2) Place samples in box with lid to fit in a high velocity shaking apparatus.

(3) Secure the box in the shaking apparatus with extra lid and cardboard to ensure a tight fit. Grind for one minute. Remove box. Rotate 180° and grind for an additional minute.

(4) Add 500 μL of extraction buffer (100 mM Tris 8.0, 10 mM EDTA, 1% Sarkosyl)

(5) Vortex tubes (6) Place tubes in a 90° C. dry bath. Incubate samples for 30 minutes.

(7) Remove tubes from bath and cool on ice >5 minutes.

(8) Centrifuge sample at 10,000 rpm for 5 minutes at room temperature.

(9) 1 μL of a 1:20 dilution of the supernatant serves as template for PCR. Diluted samples should be stored at minus 20° C. and kept on ice for all manipulations.

Maize tissue samples extracted by the above method and used in the following Examples are listed in Table 3.

TABLE 3

Maize Tissue Samples[1]

| Sample Designation | Tissue |
|---|---|
| H-5 | Husk |
| H-9 | Husk |
| SBP-2 | Husk associated with Sap Beetle |

[1]Samples were collected in Mason County, Illinois, USA and received from Pat Dowd, USDA-ARS, Peoria, IL

Example 3

Polymerase Chain Reaction (PCR) Amplification

Polymerase chain reactions are performed with the GeneAmp Kit from Perkin-Elmer (Foster City, Calif.; part no. N808-0009) using 50 mM KCl, 2.5 mM $MgCl_2$, 10 mM Tris-HCl, pH8.3, containing 200 μM of each dTTP, dATP, dCTP, and dGTP in 25 μL reactions containing 25 pmol each primer, 1.25 units of Taq polymerase and 10 ng of genomic DNA. Reactions are run for 30–40 cycles of 15 s at 94° C., 15 s at 50° C.–70° C., and 45 s at 72° C. in a Perkin-Elmer Model 9600 or 9700 thermal cycler. The products are analyzed by loading 10 μl of each PCR sample on a 1.0% agarose gel and electrophoresing.

Example 4

Synthesis and Purification of Oligonucleotides

Oligonucleotides (primers) are synthesized by, for example, either Integrated DNA Technologies (Coralville, Iowa) or Midland Certified Reagent Company (Midland, Tex.).

Example 5

Design of Species-specific PCR Primers

Sequences are obtained from the GenBank database of the National Center for Biotechnology Information (www.ncbi.nlm.nih.gov) for partial sequence listings of small subunit ribosomal RNA and mitochondrial gene for *F. verticillioides* (SEQ ID NO: 1); *F. proliferatum* (SEQ ID NO: 2); *F. graminearum* (syn. *Gibberella zeae*) (SEQ ID NO: 3); and *F. subglutinans* (SEQ ID NO: 4). A multiple sequence alignment is made of these sequences. The alignment is analyzed for divergences among the four sequences. The divergences permit the development of primers that will specifically amplify one of the four target sequences in PCR reactions. Oligonucleotide primers are designed to target regions that contain the greatest differences in sequence among the species analyzed (Table 4). FSUB1 (SEQ ID NO: 15), FSUB2 (SEQ ID NO: 16), and FSUB3 (SEQ ID NO: 17) are designed to target the mitochondrial small subunit (mtSSU) rDNA of *Fusarium subglutinans*. FPRO1 (SEQ ID NO: 20) is designed to target the mtSSU rDNA of *Fusarium proliferatum*. The mtSSU rDNA of *Fusarium verticillioides* is the target of primers FVERT1 (SEQ ID NO: 18) and FVERT2 (SEQ ID NO: 19). These primers may be used in combination with primers FCORN1 (SEQ ID NO: 13) and FCORN2 (SEQ ID NO: 14) that target mtSSU rDNA conserved between the three targeted species of *Fusarium*.

Similarly, ITS region rDNA sequence listings for *F. subglutinans* (SEQ ID NO: 5), *F. graminearum* (syn. *Gibberella zeae*) (SEQ ID NO: 6), *F. proliferatum* (SEQ ID NO: 7), and *F. verticillioides* (syn. *F. verticillioides*) (SEQ ID NO: 8) were obtained. An alignment of ITS region sequences is used as above to develop specific primers. In addition, the published ribosomal gene-specific primers ITS1, ITS2, ITS3 and ITS4 (White et al., 1990; In: PCR Protocols; Eds.: Innes et al. pages 315–322) are synthesized for testing in combination with the primers specific for the ITS regions. Primers FPRO2 and FPRO3 target the nuclear rDNA ITS 2 region of *Fusarium proliferatum*. They maybe used with ITS1, the conserved fungal nuclear rDNA primer targeting the ITS1 region. The species-specific primers as well as the conserved fungal ITS region primers are shown in Table 4.

TABLE 4

Primers Designed for Detection of Fusarium Ear Rot Pathogens
*Fusarium subglutinans*, *F. proliferatum*, and *F. verticilioides*

| Name | Oligo Sequence (5' → 3') | Target | Identifier |
|---|---|---|---|
| ITS1 | TCCGTAGGTGAACCTGCGG | Fungal Nuclear rDNA ITS region | SEQ-ID-NO:9 |
| ITS2 | GCTGCGTTCTTCATCGATGC | Fungal Nuclear rDNA ITS region | SEQ-ID-NO:10 |
| ITS3 | GCATCGATGAAGAACGCAGC | Fungal Nuclear rDNA ITS region | SEQ-ID-NO:11 |
| ITS4 | TCCTCCGCTTATTGATATGC | Fungal Nuclear rDNA ITS region | SEQ-ID-NO:12 |
| FCORN1 | GCAACTTGGAGAAGTGGCAAG | *Fusarium sp.* Mitochondrial small subunit rDNA | SEQ-ID-NO:13 |
| FCORN2 | AAGTCTTCCAGTATGGGGAG | *Fusarium sp.* Mitochondrial small subunit rDNA | SEQ-ID-NO:14 |
| FSUB1 | GTCCGATATCTTTAGGAGGC | *Fusarium subglutinans* Mitochondrial small subunit rDNA | SEQ-ID-NO:15 |
| FSUB2 | TCAACTAGACTACCAACTCAG | *Fusarium subglutinans* Mitochondrial small subunit rDNA | SEQ-ID-NO:16 |
| FSUB3 | CAAATCTAAGGCTGGCTTGTA | *Fusarium subglutinans* Mitochondrial small subunit rDNA | SEQ-ID-NO:17 |
| FVERT1 | TGGTGGACTAGTCTGAATCC | *Fusarium verticillioides* Mitochondrial small subunit rDNA | SEQ-ID-NO:18 |
| FVERT2 | TCAACTACGACTAACCCACC | *Fusarium verticillioides* Mitochondrial small subunit rDNA | SEQ-ID-NO:19 |
| FPRO1 | TAAACTAACTCAACTAGACGAG | *Fusarium proliferatum* Mitochondrial small subunit rDNA | SEQ-ID-NO:20 |

TABLE 4-continued

Primers Designed for Detection of Fusarium Ear Rot Pathogens
*Fusarium subglutinans, F. proliferatum,* and *F. verticilioides*

| Name | Oligo Sequence (5' → 3') | Target | Identifier |
|---|---|---|---|
| FPRO2 | GATTTCGGGGCCGGCTTGC | *Fusarium proliferatum* nuclear rDNA ITS region | SEQ-ID-NO:21 |
| FPRO3 | CGCAAGGGCTCGCCGATC | *Fusarium proliferatum* nuclear rDNA ITS region | SEQ-ID-NO:22 |
| MS1 | CAGCAGTCAAGAATATTAGTCA ATG | Fungal mitochondrial small subunit rDNA region | SEQ-ID-NO:23 |
| MS2 | GCGGATTATCGAATTAAATAAC | Fungal mitochondrial small subunit rDNA region | SEQ-ID-NO:24 |

Example 6

Determination of Primer Specificity to Purified Fungal Genomic DNA

PCRs are performed according to Example 3 using different primer combinations (Table 5) in an attempt to amplify single specific fragments. Specific PCR amplification products are produced from primers designed from the mitochondrial small subunit rDNA or the nuclear rDNA ITS regions of each fungal strain of interest.

In an initial screen for specificity, PCR reaction mixtures are made according to Example 3 for each of the primer combinations in Table 5. These are run against a negative control (no DNA added), a healthy maize tissue control (prepared in Example 2A) to test for background amplification, and 10 ng of DNA from the following isolates in Table 1: *Fusarium moniliforme* M-3120; *Fusarium subglutinans* M-3693; *Fusarium subglutinans* M-3696; *Fusarium proliferatum* M-5991; *Fusarium culmorum* R-5126; *Fusarium graminearum* R-8637; *Microdochium nivale* 15N1; *M. nivale* var. *majus* 93; *Fusarium poae* T-427; and *Fusarium avenaceum* 64452 prepared as described in Example 1.

TABLE 5

Possible Combinations of PCR Primers for the Specific Amplification of
*Fusarium subglutinans, F. verticillioides,* and *F. proliferatum.*

| Target Pathogen | 5' primer | 3' primer | Approximate Product Size (bp) |
|---|---|---|---|
| *Fusarium subglutinans* | FCORN1 (SEQ ID NO:13) | FSUB2 (SEQ ID NO:16) | 513 |
| *Fusarium subglutinans* | FCORN (SEQ ID NO:14) | FSUB2 (SEQ ID NO:16) | 495[1] |
| *Fusarium subglutinans* | FSUB1 (SEQ ID NO:15) | FSUB2 (SEQ ID NO:16) | 456 |
| *Fusarium subglutinans* | FCORN1 (SEQ ID NO:13) | FSUB3 (SEQ ID NO:17) | 559[2] |
| *Fusarium subglutinans* | FCORN (SEQ ID NO:14) | FSUB3 (SEQ ID NO:17) | 541[3] |
| *Fusarium subglutinans* | FSUB1 (SEQ ID NO:15) | FSUB3 (SEQ ID NO:17) | 502[4] |
| *Fusarium verticillioides* | FCORN1 (SEQ ID NO:13) | FVERT1 (SEQ ID NO:18) | 544[5] |
| *Fusarium verticillioides* | FCORN2 (SEQ ID NO:14) | FVERT1 (SEQ ID NO:18) | 526 |
| *Fusarium verticillioides* | FCORN1 (SEQ ID NO:13) | FVERT2 (SEQ ID NO:19) | 505[6] |
| *Fusarium verticillioides* | FCORN2 (SEQ ID NO:14) | FVERT2 (SEQ ID NO:19) | 487 |
| *Fusarium proliferatum* | FCORN1 (SEQ ID NO:13) | FPRO1 (SEQ ID NO:20) | 520[7] |
| *Fusarium proliferatum* | FCORN2 (SEQ ID NO:14) | FPRO1 (SEQ ID NO:20) | 502 |
| *Fusarium proliferatum* | ITS1 (SEQ ID NO:9) | FPRO2 (SEQ ID NO:21) | 385[8] |
| *Fusarium proliferatum* | ITS1 (SEQ ID NO:9) | FPRO3 (SEQ ID NO:22) | 370[9] |
| *Fusarium proliferatum* | ITS3 (SEQ ID NO:11) | FPRO2 (SEQ ID NO:21) | 180 |
| *Fusarium proliferatum* | ITS3 (SEQ ID NO:11) | FPRO3 (SEQ ID NO:22) | 160 |
| *Fungal ITS region* | ITS1 (SEQ ID NO:9) | ITS4 (SEQ ID NO:12) | 530 |

TABLE 5-continued

Possible Combinations of PCR Primers for the Specific Amplification of *Fusarium subglutinans, F. verticillioides,* and *F. proliferatum.*

| Target Pathogen | 5' primer | 3' primer | Approximate Product Size (bp) |
|---|---|---|---|
| *Fungal ITS region* | ITS1 (SEQ ID NO:9) | ITS2 (SEQ ID NO:10) | 210 |
| *Fungal ITS region* | ITS3 (SEQ ID NO:9) | ITS4 (SEQ ID NO:12) | 330 |

[1]Amplifies *F. subglutinans* target well, but produces a high molecular weight nonspecific with *F. culmorum* and *F. graminearum*
[2]Did not react with one isolate of *F. subglutinans* target DNA, produced a high molecular weight nonspecific with *F. culmorum*
[3]Amplifies *F. subglutinans* target well, but produces a high molecular weight nonspecific with *F. culmorum*
[4]Amplifies *F. subglutinans* target well, but produces a low molecular weight nonspecific with all DNAs tested and the negative control
[5]Amplifies *F. verticillioides* target to a lesser extent than other primers tested and produces a low molecular weight nonspecific with the negative control
[6]Amplifies *F. verticillioides* target well, but also amplifies a product with *F. proliferatum*
[7]Amplifies *F. proliferatum* target well, but produces a nonspecifics with *Michrodochium nivale* var. majus and *F. culmorum*
[8]Amplifies from one *F. proliferatum* isolate but not from others and produces nonspecifics with all isolates tested in the initial screen with the exception of *F. poae* and *F. avenaceum*
[9]Amplifies *F. proliferatum* target well, but produces a nonspecifics with *F. subglutinans* M3696 and *F. verticillioides*

When visualized on an ethidium bromide stained gel, several primer pairs amplified single products from target DNA with all other reactions (negative control, maize background, and other fungal DNAs) free of both specific and nonspecific reaction products. The primer pairs that give the best amplification for their specific targets with no cross-amplification are summarized in Table 6. See footnotes (Table 5) for information on those primer pairs that amplified target DNA but with less satisfactory results in terms of specificity.

TABLE 6

PCR Primer Pairs Providing Specific and Sensitive Amplification of Target DNA for *Fusarium subglutinans, F. verticillioides,* and *F. proliferatum* PCR Assays.

| Target Pathogen | 5'primer | 3'primer | Approximate Product Size (bp) |
|---|---|---|---|
| *Fusarium subglutinans* | FSUB1 (SEQ ID NO:15) | FSUB2 (SEQ ID NO:16) | 456 |
| *Fusarium subglutinans* | FCORN1 (SEQ ID NO:13) | FSUB2 (SEQ ID NO:16) | 513 |
| *Fusarium verticillioides* | FCORN2 (SEQ ID NO:14) | FVERT1 (SEQ ID NO:18) | 526 |
| *Fusarium verticillioides* | FCORN2 (SEQ ID NO:14) | FVERT2 (SEQ ID NO:19) | 487 |
| *Fusarium proliferatum* | FCORN2 (SEQ ID NO:14) | FPRO1 (SEQ ID NO:20) | 502 |

Example 7

Validation of *Fusarium subglutinans, F. verticillioides*, and *F. proliferatum* PCR Assays Showing Reactivity of Multiple Isolates for a Given Target One of the primer pairs in Table 6 is chosen for each target DNA for further characterization and testing: FSUB 1 and FSUB2 for *Fusarium subglutinans*, FCORN2 and FVERT1 for *F. verticillioides*, and FCORN2 with FPRO1 for *F. proliferatum*. Each is run in PCR mastermixes against DNAs from a panel of fungal species (all isolates in Table 1) prepared as in Example 1. Products are visualized on an ethidium bromide stained gel. Results are scored as either positive (+) or negative (–) for the amplification of target DNA with any product visible, of the correct size, being considered a positive and with nonspecifics recorded if present. Results of each of these tests are shown in Tables 7–9. Table 7 shows that primers FSUB1 (SEQ ID NO: 15) and FSUB2 (SEQ ID NO: 16), when prepared in PCR reactions as described in Example 3, amplify target DNA from only the isolates identified as *Fusarium subglutinans*. The primers do not react with isolates of *Fusarium proliferatum, F. verticillioides*, or with other fungal species known to infect or also shows that the *F. subglutinans* specific primers DNA described in Example 2A.

TABLE 7

Results of *F. subglutinans* PCR Assay Against a Panel of Ear Rot Pathogen DNAs and a Maize Background Check.

| Fungal species | Isolate | Isolation | Geographic Origin | *F. subglutinans* PCR Result |
|---|---|---|---|---|
| *Fusarium proliferatum* | M-5991 | Swine Feed | Iowa, USA | – |
| *Fusarium proliferatum* | 94-041 | Maize | Iowa, USA | – |
| *Fusarium proliferatum* | 94-066 | Maize | Iowa, USA | – |
| *Fusarium proliferatum* | 94-129 | Maize | Iowa, USA | – |
| *Fusarium proliferatum* | 95-122 | Maize | Iowa, USA | – |
| *Fusarium proliferatum* | 95-135 | Maize | Iowa, USA | – |
| *Fusarium proliferatum* | 95-289 | Maize | Iowa, USA | – |
| *Fusarium proliferatum* | M-1231 | Rice | Phillipines | – |
| *Fusarium proliferatum* | M-1264 | Rice | Sierra Leone | – |
| *Fusarium proliferatum* | M-1329 | Rice | California, USA | – |
| *Fusarium proliferatum* | M-3744 | Rice | Australia | – |
| *Fusarium proliferatum* | M-5167 | Rice | Iran | – |
| *Fusarium proliferatum* | M-5587 | Date Palm | Iraq | – |
| *Fusarium proliferatum* | M-5605 | | Poland | – |
| *Fusarium proliferatum* | M-6173 | Rice | Malaysia | – |
| *Fusarium proliferatum* | M-6471 | Maize | Kansas, USA | – |
| *Fusarium proliferatum* | M-8510 | Rice | Nepal, USA | – |
| *Fusarium verticillioides* | NRRL 6396 | Chicken Feed | Arkansas, USA | – |
| *Fusarium verticillioides* | NRRL 13563 | *Pinus taeda* | North Carolina, USA | – |
| *Fusarium verticillioides* | M-3120 | Maize | California, USA | – |
| *Fusarium verticillioides* | M-3125 | Maize | California, USA | – |
| *Fusarium subglutinans* | NRRL 13588 | Maize | Iowa, USA | – |
| *Fusarium subglutinans* | NRRL 13599 | Maize | Zambia | + |
| *Fusarium subglutinans* | NRRL 20844 | Maize | Germany | + |
| *Fusarium subglutinans* | M3693 | Maize | Iowa, USA | + |
| *Fusarium subglutinans* | M3696 | Maize | Iowa, USA | + |
| *Fusarium sambucinium-sulphureum* | R-6380 | Maize | Iowa, USA | – |
| *Fusarium sporotrichioides* | 3299 | | | – |
| *Fusarium culmorum* | R-5126 | | Minnesota, USA | – |
| *Fusarium graminearum* | R-8637 | | Settat, Morocco | – |
| *Microdochium nivale* | 15N1 | | United Kingdom | – |
| *Microdochium nivale* var. *majus* | #093 | | | – |
| *Fusarium poae* | T-427 | | Pennsylvannia, USA | – |
| *Fusarium avenaceum* | ATCC 64452 | | Poland | – |
| *Diplodia maydis* | 5139 | | | |
| *Macrophomina phaseolina* | MP97 | | | – |
| *Aspergillus flavus* | 3557 | | | – |
| *Kabatiella zeae* | 18594 | Maize | Wisconsin, USA | – |
| *Cercospora zeae-maydis* | 69281L | | | – |
| *Cercospora zeae-maydis* | 26158 | Maize | New York, USA | – |
| *Puccinia sorghi* | VA | | | |
| *Helminthosporium maydis* | 24772 | Maize | North Carolina, USA | – |
| *Helminthosporium maydis* | 11534 | Maize | Maryland, USA | – |
| *Helminthosporium carbonum* | 16185 | Maize | Virginia, USA | – |
| *Helminthosporium carbonum* | 24962 | Maize | Illinois, USA | – |
| *Helminthosporium turcicum* | 26306 | Maize | Illinois, USA | – |
| *Fusarium culmorum* | 62215 | Wheat seed | Switzerland | – |
| *Fusarium culmorum* | R-5106 | | Darling Downs, Australia | – |
| 1999 Maize sample #1 | — | — | Iowa, USA | – |

Table 8 shows that primers FCORN2 (SEQ ID NO: 14) and FPRO1 (SEQ ID NO: 20), when prepared in PCR reactions as described in Example 3, amplify target DNA from only the isolates identified as *Fusarium proliferatum* and with all isolates in this study that were identified as *F. proliferatum*. The primers do not react with maize DNA (1999 Maize sample #1 or with other fungal species know to infect or colonize maize tissue including *F. verticillioides* and *F. subglutinans*

TABLE 8

Results of *F. proliferatum* PCR Assay Against a Panel of Ear Rot Pathogen DNAs and a Maize Background Check.

| Fungal species | Isolate | Isolation | Geographic Origin | *F. proliferatum* PCR Result |
|---|---|---|---|---|
| *Fusarium proliferatum* | M-5991 | Swine Feed | Iowa, USA | + |
| *Fusarium proliferatum* | 94-041 | Maize | Iowa, USA | + |
| *Fusarium proliferatum* | 94-066 | Maize | Iowa, USA | + |
| *Fusarium proliferatum* | 94-129 | Maize | Iowa, USA | + |
| *Fusarium proliferatum* | 95-122 | Maize | Iowa, USA | + |
| *Fusarium proliferatum* | 95-135 | Maize | Iowa, USA | + |
| *Fusarium proliferatum* | 95-289 | Maize | Iowa, USA | + |
| *Fusarium proliferatum* | M-1231 | Rice | Phillipines | + |
| *Fusarium proliferatum* | M-1264 | Rice | Sierra Leone | + |
| *Fusarium proliferatum* | M-1329 | Rice | California, USA | + |
| *Fusarium proliferatum* | M-3744 | Rice | Australia | + |
| *Fusarium proliferatum* | M-5167 | Rice | Iran | + |
| *Fusarium proliferatum* | M-5587 | Date Palm | Iraq | + |
| *Fusarium proliferatum* | M-5605 | | Poland | + |
| *Fusarium proliferatum* | M-6173 | Rice | Malaysia | + |
| *Fusarium proliferatum* | M-6471 | Maize | Kansas, USA | + |
| *Fusarium proliferatum* | M-8510 | Rice | Nepal, USA | + |
| *Fusarium verticillioides* | NRRL 6396 | Chicken Feed | Arkansas, USA | – |
| *Fusarium verticillioides* | NRRL 13563 | *Pinus taeda* | North Carolina, USA | – |
| *Fusarium verticillioides* | M-3120 | Maize | California, USA | – |
| *Fusarium verticillioides* | M-3125 | Maize | California, USA | – |
| *Fusarium subglutinans* | NRRL 13588 | Maize | Iowa, USA | – |
| *Fusarium subglutinans* | NRRL 13599 | Maize | Zambia | – |
| *Fusarium subglutinans* | NRRL 20844 | Maize | Germany | – |
| *Fusarium subglutinans* | M3693 | Maize | Iowa, USA | – |
| *Fusarium subglutinans* | M3696 | Maize | Iowa, USA | – |
| *Fusarium sambucinium-sulphureum* | R-6380 | Maize | Iowa, USA | – |
| *Fusarium sporotrichioides* | 3299 | | | – |
| *Fusarium culmorum* | R-5126 | | Minnesota, USA | – |
| *Fusarium graminearum* | R-8637 | | Settat, Morocco | – |
| *Microdochium nivale* | 15N1 | | United Kingdom | – |
| *Microdochium nivale* var. *majus* | #093 | | | – |
| *Fusarium poae* | T-427 | | Pennsylvannia, USA | – |
| *Fusarium avenaceum* | ATCC 64452 | | Poland | – |
| *Diplodia maydis* | 5139 | | | – |
| *Macrophomina phaseolina* | MP97 | | | – |
| *Aspergillus flavus* | 3557 | | | – |
| *Kabatiella zeae* | 18594 | Maize | Wisconsin, USA | – |
| *Cercospora zeae-maydis* | 69281L | | | – |
| *Cercospora zeae-maydis* | 26158 | Maize | New York, USA | – |
| *Puccinia sorghi* | VA | | | – |
| *Helminthosporium maydis* | 24772 | Maize | North Carolina, USA | – |
| *Helminthosporium maydis* | 11534 | Maize | Maryland, USA | – |
| *Helminthosporium carbonum* | 16185 | Maize | Virginia, USA | – |
| *Helminthosporium carbonum* | 24962 | Maize | Illinois, USA | – |
| *Helminthosporium turcicum* | 26306 | Maize | Illinois, USA | – |
| *Fusarium culmorum* | 62215 | Wheat seed | Switzerland | – |
| *Fusarium culmorum* | R-5106 | | Darling Downs, Australia | – |
| 1999 Maize sample #1 | — | — | Iowa, USA | – |

The primers FCORN2 (SEQ ID NO: 14) and FVERT1 (SEQ ID NO: 18) were run against the same DNA preparations of fungal isolates and maize tissue that were tested using the *F. subglutinans* and *F. proliferatum* specific primers (results in Tables 7 and 8, respectively). The *F. verticillioides* specific primers, when prepared in PCR reactions as described in Example 3, amplify target DNA from only the isolates identified as *Fusarium verticillioides* (Table 9). The primers do not react with isolates of *Fusarium subglutinans, F proliferatum*, or with other fungal species known to infect or colonize maize tissue. Table 9 also shows that FCORN2 and FVERT1 do not react with a preparation of maize DNA.

TABLE 9

Results of *F. verticillioides* PCR Assay Against a Panel of Ear Rot Pathogen DNAs and a Maize Background Check.

| Fungal species | Isolate | Isolation | Geographic Origin | *F. verticillioides* PCR Result |
|---|---|---|---|---|
| *Fusarium proliferatum* | M-5991 | Swine Feed | Iowa, USA | – |
| *Fusarium proliferatum* | 94-041 | Maize | Iowa, USA | – |
| *Fusarium proliferatum* | 94-066 | Maize | Iowa, USA | – |
| *Fusarium proliferatum* | 94-129 | Maize | Iowa, USA | – |
| *Fusarium proliferatum* | 95-122 | Maize | Iowa, USA | – |
| *Fusarium proliferatum* | 95-135 | Maize | Iowa, USA | – |
| *Fusarium proliferatum* | 95-289 | Maize | Iowa, USA | – |
| *Fusarium proliferatum* | M-1231 | Rice | Phillipines | – |
| *Fusarium proliferatum* | M-1264 | Rice | Sierra Leone | – |
| *Fusarium proliferatum* | M-1329 | Rice | California, USA | – |
| *Fusarium proliferatum* | M-3744 | Rice | Australia | – |
| *Fusarium proliferatum* | M-5167 | Rice | Iran | – |
| *Fusarium proliferatum* | M-5587 | Date Palm | Iraq | – |
| *Fusarium proliferatum* | M-5605 | | Poland | – |
| *Fusariuin proliferatum* | M-6173 | Rice | Malaysia | – |
| *Fusarium proliferatum* | M-6471 | Maize | Kansas, USA | – |
| *Fusarium proliferatum* | M-8510 | Rice | Nepal, USA | – |
| *Fusarium verticillioides* | NRRL 6396 | Chicken Feed | Arkansas, USA | + |
| *Fusarium verticillioides* | NRRL 13563 | *Pinus taeda* | North Carolina, USA | + |
| *Fusarium verticillioides* | M-3120 | Maize | California, USA | + |
| *Fusarium verticillioides* | M-3125 | Maize | California, USA | + |
| *Fusarium subglutinans* | NRRL 13588 | Maize | Iowa, USA | – |
| *Fusarium subglutinans* | NRRL 13599 | Maize | Zambia | – |
| *Fusarium subglutinans* | NRRL 20844 | Maize | Germany | – |
| *Fusarium subglutinans* | M3693 | Maize | Iowa, USA | – |
| *Fusarium subglutinans* | M3696 | Maize | Iowa, USA | – |
| *Fusarium sambucinium-sulphureum* | R-6380 | Maize | Iowa, USA | – |
| *Fusarium sporotrichioides* | 3299 | | | – |
| *Fusarium culmorum* | R-5126 | | Minnesota, USA | – |
| *Fusarium graminearum* | R-8637 | | Settat, Morocco | – |
| *Microdochium nivale* | 15N1 | | United Kingdom | – |
| *Microdochium nivale* var. *majus* | #093 | | | – |
| *Fusarium poae* | T-427 | | Pennsylvannia, USA | – |
| *Fusarium avenaceum* | ATCC 64452 | | Poland | – |
| *Diplodia maydis* | 5139 | | | – |
| *Macrophomina phaseolina* | MP97 | | | – |
| *Aspergillus flavus* | 3557 | | | – |
| *Kahatiella zeae* | 18594 | Maize | Wisconsin, USA | – |
| *Cercospora zeae-maydis* | 69281L | | | – |
| *Cercospora zeae-maydis* | 26158 | Maize | New York, USA | – |
| *Puccinia sorghi* | VA | | | |
| *Helminthosporium maydis* | 24772 | Maize | North Carolina, USA | – |
| *Helminthosporium maydis* | 11534 | Maize | Maryland, USA | – |
| *Helminthosporium carbonum* | 16185 | Maize | Virginia, USA | – |
| *Helminthosporium carbonum* | 24962 | Maize | Illinois, USA | – |
| *Helminthosporium turcicum* | 26306 | Maize | Illinois, USA | – |
| *Fusarium culmorum* | 62215 | Wheat seed | Switzerland | – |
| *Fusarium culmorum* | R-5106 | | Darling Downs, Australia | – |
| 1999 Maize sample #1 | — | — | Iowa, USA | – |

In summary, assays using FSUB1 and FSUB2 for *Fusarium subglutinans*, FCORN2 and FVERT1 for *F. verticillioides*, and FCORN2 with FPRO 1 for *F. proliferatum* amplified DNAs only from target species for each PCR assay. No cross-reactivity with any of the other DNAs was observed. FSUB1 when used with FSUB2 in PCR reactions, when prepared as in Example 3, amplify only the isolates in Table 1 identified as *Fusarium subglutinans*. Likewise, primers FCORN2 and FVERT 1 amplify products only with isolates identified as the target *Fusarium verticillioides* and primers FCORN2 and FPRO1 amplify from *Fusarium proliferatum* isolates only. No cross-reactivity is observed among preparations of non-target DNA from maize and other fungal pathogens. Furthermore, nonspecific amplification products are absent in all reactions performed.

Example 8

Use of *Fusarium subglutinans, F. verticillioides*, and *F. proliferatum* PCR Assays for Determination of Fungal Species Cultured from Field Samples The maize ear rot PCR assays documented in the above examples are used to establish the speciation of unknown ear rot isolates cultured from field-grown maize in Stanton, Minn., USA (Table 2). PCRs are performed as described in Example 3 using optimal primer pairs (FSUB1 and FSUB2 for *Fusarium subglutinans*, FCORN2 and FVERT1 for *F. verticillioides*, and FCORN2 with FPRO 1 for *F. proliferatum*) against DNA from the field isolates prepared as described in Example 1. Products are visualized on an ethidium bromide stained gel. Results are scored as either positive (+) or negative (−) for the amplification of target DNA. Any PCR product visible, of the correct size, is considered a positive and nonspecifics are recorded if present. Results of each of these tests are shown in Tables 10–12.

TABLE 10

Results of *F. subglutinans* PCR Assays Against Isolates Collected from Field-grown Maize.

| Isolate | *F. subglutinans* PCR Result | Isolate | *F. subglutinans* PCR Result |
|---|---|---|---|
| Fm001 | − | Fm042 | − |
| Fm002 | − | Fm043 | − |
| Fm003 | + | Fm044 | − |
| Fm004 | − | Fm045 | − |
| Fm005 | − | Fm046 | − |
| Fm006 | − | Fm047 | − |
| Fm007 | − | Fm048 | − |
| Fm008 | − | Fm049 | − |
| Fm009 | − | Fm050 | − |
| Fm010 | − | Fm051 | − |
| Fm011 | − | Fm052 | − |
| Fm012 | − | Fm053 | − |
| Fm013 | − | Fm054 | − |
| Fm014 | − | Fm055 | − |
| Fm034 | − | Fm056 | − |
| Fm035 | − | BC3SO 189 | − |
| Fm036 | − | Fsub1 | + |
| Fm037 | − | Fsub2 | + |
| Fm041 | − | Fsub3 | + |
| | | Fsub4 | + |

Five of the forty-one isolates cultured from field-grown maize react with the *Fusarium subglutinans* primers.

TABLE 11

Results of *F. proliferatum* PCR Assays Against Isolates Collected from Field-grown Maize.

| Isolate | *F. proliferatum* PGR Result | Isolate | *F. proliferatum* PCR Result |
|---|---|---|---|
| Fm001 | − | Fm042 | − |
| Fm002 | − | Fm043 | − |
| Fm003 | − | Fm044A | + |

TABLE 11-continued

Results of *F. proliferatum* PCR Assays Against Isolates Collected from Field-grown Maize.

| Isolate | *F. proliferatum* PGR Result | Isolate | *F. proliferatum* PCR Result |
|---|---|---|---|
| Fm004 | − | Fm045 | − |
| Fm005 | − | Fm046 | − |
| Fm006 | − | Fm047A | + |
| Fm007 | − | Fm048 | − |
| Fm008 | − | Fm049 | − |
| Fm009 | − | Fm050 | − |
| Fm010 | + | Fm051 | − |
| Fm011 | − | Fm052 | − |
| Fm012 | − | Fm053 | − |
| Fm013 | − | Fm054 | − |
| Fm014 | + | Fm055 | − |
| Fm034 | − | Fm056 | − |
| Fm035 | − | BC3SO 189 | − |
| Fm036 | − | Fsub1 | − |
| Fm037A | + | Fsub2 | − |
| Fm041 | − | Fsub3 | − |
| | | Fsub4 | − |

The *Fusarium proliferatum* specific primers react with five of the forty-one isolates cultured from field-grown maize.

TABLE 12

Results of *F. verticillioides* PCR Assay Against Isolates Collected from Field-grown Maize.

| Isolate | *F. verticillioides* PGR Result | Isolate | *F. verticillioides* PCR Result |
|---|---|---|---|
| Fm001 | + | Fm042 | + |
| Fm002 | + | Fm043 | + |
| Fm003 | − | Fm044 | − |
| Fm004 | + | Fm045 | + |
| Fm005 | + | Fm046 | + |
| Fm006 | + | Fm047 | − |
| Fm007 | + | Fm048 | + |
| Fm008 | + | Fm049 | + |
| Fm009 | + | Fm050 | + |
| Fm010 | − | Fm051 | + |
| Fm011 | + | Fm052 | + |
| Fm012 | + | Fm053 | + |
| Fm013 | − | Fm054 | + |
| Fm014 | − | Fm055 | − |
| Fm034 | + | Fm056 | + |
| Fm035 | + | BC3SO 189 | − |
| Fm036 | + | Fsub1 | − |
| Fm037 | − | Fsub2 | − |
| Fm041 | + | Fsub3 | − |
| | | Fsub4 | − |

Twenty-eight of the isolates cultured from field-grown maize were identified as *Fusarium verticillioides* with the species-specific PCR primers FCORN2 and FVERT1. For the forty-one isolates tested, none react with more than one of the three tests. These experiments demonstrate the utility of the diagnostic PCR primers for characterizing isolates of maize ear rot.

Example 9

Use of *Fusarium subglutinans, F. verticillioides*, and *F. proliferatum* PCR Assays for Detection and Differentiation of Fungal Species Infecting Husk Tissues Collected from Field-grown Maize The maize ear rot PCR assays are used to establish the speciation of ear rot pathogens present in husk tissue samples taken from field-grown maize (Table 2). PCRs are performed as described in Example 3 using FSUB1 and FSUB2 for *Fusarium subglutinans*, FCORN2 and FVERT 1 for *F. verticillioides*, and FCORN2 with FPRO1 for *F. proliferatum* against DNA from the field isolates prepared as in Example 2B. Products are visualized on an ethidium bromide stained gel. Results are scored as either positive (+) or negative (–) for the amplification of target DNA. Products are compared to a molecular size marker and positive controls on the gel to determine that the products scored are of the correct size and any nonspecific amplification products are recorded if present. Results of the *Fusarium subglutinans* test are shown in Table 13.

TABLE 13

Results of *F. subglutinans* Assay Against Various Maize Tissues

| Sample Designation | Tissue | *F. subglutinans* PCR Result |
|---|---|---|
| H-5 | Husk | + |
| H-9 | Husk | + |
| SBP-2 | Husk | + |

The three maize tissues tested are identified as positive for the presence of *Fusarium subglutinans* target DNA. *Fusarium proliferatum* and *F. verticillioides* tests are also run against these husk tissues. No target DNA is detected in the maize tissues using the *F. proliferatum* or *F. verticillioides* assays. The results of these experiments show the utility of the maize ear rot assays in identifying and distinguishing species present in maize tissue samples without having to first culture the organism out of the tissue. The primers in Example 6 can be used in PCR assays to directly characterize extractions of maize tissue.

Example 10

Determination of Primer Specificity to Purified Fungal Genomic DNA Using MS1 or MS2 primer Combinations Primers MS1 and MS2 from the literature are designed to amplify mitochondrial small subunit rDNA. The MS1 priming site lies upstream of the reverse primers FSUB2, FSUB3, FVERT1, FVERT2, and FPRO1. Using the conserved MS1 primer in combination with 3' primers specific to a fungus such as a *Fusarium* spp. in polymerase chain reactions performed as in Example 3 produces am assau ised tp detect the specific fungus. For example, MS1 is combined with a 3' primer listed in Table 5 such as: FSUB2 or FSUB3 to detect *F. subglutinans*; FVERT1 or FVERT2 to detect *F. verticillioides*; and FPRO1 to detect *F. proliferatum.*

Similarly, the MS2 reverse primer in combination with 5' primers specific to a fungus such as *Fusarium* spp. are used to detect one or more specific fungi in PCR reactions performed as in Example 3. For example, MS2 is combined with a 5' primer listed in Table 5 such asFSUB1 to detect *F. subglutinans*; and FCORN1 or FCORN2 to *Fusarium* spp. in general. Such an assay for *Fusarium* spp. could have utility in situations where detection of *Fusarium* spp. without differentiation of the species present is desired.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Numerous patents, applications and references are discussed or cited within this specification, and all are incorporated by reference in their entireties.

What is claimed is:

1. A method for the detection of a fungal pathogen, comprising the steps of:

(a) isolating DNA from a plant leaf infected with a pathogen;

(b) subjecting said DNA to polymerase chain reaction amplification using a pair of primers wherein each primer has sequence identity with at least 10 contiguous nucleotides of a mitochondrial small subunit rDNA gene from *Fusarium verticilloides* (syn. *F. moniliforne*) and wherein at least one primer comprises the nucleotide sequence of SEQ ID NOS: 13—20, 23 or 24; and (c) detecting said fungal pathogen by visualizing the product or products of said polymerase chain reaction amplification.

2. The method of claim 1, wherein the primers comprise:

(a) SEQ ID NO:14 and SEQ ID NO:18;

(b) SEQ ID NO:14 and SEQ ID NO:19; or (c) SEQ ID NO: 14 and SEQ ID NO:20.

* * * * *

SEQUENCE LISTING

```
<160> NUMBER OF SEQ ID NOS: 24
<210> SEQ ID NO 1
<211> LENGTH: 682
<212> TYPE: DNA
<213> ORGANISM: Fusarium verticillioides (syn. F. moniliforme)

<400> SEQUENCE: 1

gctaacggct gaactggcaa cttggagaag tggcaagtct tccagtatgg ggagcaaaac     60

agctatgggt caagtccgat atctttagga gaagtcttat tgtgagggcg agttttataa    120

caccatagga ctggccgccc catatgaaaa gattatatta gaattgaatg aagctttgtt    180

tatatattga taatgacagt atatatatcg tgtcttgact aattgcgtgc cagcagtcgc    240

ggtaatacgt aagagactag tgttattcat cttaattagg tttaaagggt acccagacgg    300

tcaatatagc ttataaaatg ttagtacttg actagagttt tatgtaagag ggcagtactt    360

gaggaggaga gatgaaattt cgtgatacca aagggactct gtaaaggcga aggcagccct    420

ctatgtaaaa actgacgttg aaggacgaag gcacagagaa caaacaggat tagataccca    480

agtagtcttt gcagtaaatg atgaatgcca taggttagat gggtgggtta gtcgtagttg    540

agttagttta gcaaactaat ggattcagac tagtccacca tatatttggt ctataaatga    600

aagtgtaagc atttcacctc aagagtaatg tggcaacgca ggaactgaaa tcactagacc    660

gtttctgaca ccagtagtga ag                                             682
```

-continued

<210> SEQ ID NO 2
<211> LENGTH: 689
<212> TYPE: DNA
<213> ORGANISM: Fusarium proliferatum

<400> SEQUENCE: 2

```
gctaacggct gaactggcaa cttggagaag tggcaagtct tccagtatgg ggagcaaaac     60

agctatgggt caagtctgat atctttagga ggggcgaagc tcctcttatt gtgagggcga    120

gttatataac accataggac tggccgcccc atatgaaaag attatattag aattgaatga    180

agctttgttt atatattgat aatgacagta tatatatcgt gtcttgacta attgcgtgcc    240

agcagtcgcg gtaatacgta agagactagt gttattcatc ttaattaggt ttaaagggta    300

cccagacggt caatatagct tataaaatgt tagtacttga ctagagtttt atgtaagagg    360

gcagtacttg aggaggagag atgaaatttc gtgataccaa agggactctg taaaggcgaa    420

ggcagccctc tatgtaaaaa ctgacgttga aggacgaagg cacagagaac aaacaggatt    480

agatacccaa gtagtctttg cagtaaatga tgaatgccat aggttagatg ggtgggctcg    540

tctagttgag ttagtttagc aaactaatga tctagacgag cccaccgtat atttggtcta    600

taaatgaaag tgtaagcatt tcacctcaag agtaatgtgg caacgcagga actgaaatca    660

ctagaccgtt tctgacacca gtagtgaag                                      689
```

<210> SEQ ID NO 3
<211> LENGTH: 726
<212> TYPE: DNA
<213> ORGANISM: gibberella zeae (syn. Fusarium graminearum)

<400> SEQUENCE: 3

```
gctaacggct gaactggcaa cttggagaag tggcaagtct tccagtatgg ggagcaaaca     60

gctatgggtc aagcccgata cctttaagag aagtcttatt gtgagggcga gttgtataac    120

accatagggc tggccgcccc atatgaaaag attttattag aattgaatga aactttgttt    180

atatattgat aatgacagta tatatatcgt gtcttgacta attgcgtgcc agcagtcgcg    240

gtaatacgta agagactagt gttattcatc ttaattaggt ttaaagggta cccagacggt    300

ctatatagct tataaaatgt tagtataaga ctagagtttt atgtaagagg gcagtacttg    360

aggaggagag atgaaatttc gtgataccaa agggactctg taaaggcgaa ggcagccctc    420

tatgtaaaaa ctgacgttga aggacgaagg cacagagaac aaacaggatt agatacccaa    480

gtagtctttg cagtaaatga tgaatgccat aggttagatc tatatttcta ttataataat    540

acatttctat tatttattat aaaacgcatt ccttatatag cttcgcgcta taatatattt    600

tatatatagt gcagcagaaa tttttgtatc tggtctataa atgaaagtgt aagcatttca    660

cctcaagagt aatgtggcaa cgcaggaact gaaatcacta gaccgtttct gacaccagta    720

gtgaag                                                               726
```

<210> SEQ ID NO 4
<211> LENGTH: 690
<212> TYPE: DNA
<213> ORGANISM: Fusarium subglutinans

<400> SEQUENCE: 4

```
gctaacggct gaactggcaa cttggagaag tggcaagtct tccagtatgg ggagcaaaac     60

agctatgggt caagtccgat atctttagga ggcgcgaagc tcctcttatt gtgagggcga    120
```

-continued gttttataac accataggac tggccgcccc atatgaaaag attatattag aattgaatga 180
agctttgttt atatattgat aatgacagta tatatatcgt gtcttgacta attgcgtgcc 240
agcagtcgcg gtaatacgta agagactagt gttattcatc ttaattaggt ttaaagggta 300
cccagacggt caatatagct tataaaatgt tagtacttga ctagagtttt atgtaagagg 360
gcagtacttg aggaggagag atgaaatttc gtgataccaa agggactcgg taaaggcgaa 420
ggcagccctc taggtaaaaa ctgacgttga aggacgaagg cacagagaac aaacaggatt 480
agatacccaa gtagtctttg cagtaaatga tgaatgccat aggttagatc tgagttggta 540
gtctagttga gttagtttac taaactaatg atctatacaa gccagcctta gatttggtct 600
ataaatgaaa gtgtaagcat ttcacctcaa gagtaatgtg gcaacgcagg aactgaaatc 660
actagaccgt ttctgacacc agtagtgaag 690

<210> SEQ ID NO 5
<211> LENGTH: 522
<212> TYPE: DNA
<213> ORGANISM: Fusarium subglutinans

<400> SEQUENCE: 5
tccgttggtg aaccagcgga gggatcatta ccgagtttac aactcccaaa cccctgtgaa 60
cataccaatt gttgcctcgg cggatcagcc cgctcccggt aaaacgggac ggcccgccag 120
aggaccccta aactctgttt ctatatgtaa cttctgagta aaaccataaa taaatcaaaa 180
ctttcaacaa cggatctctt ggttctggca tcgatgaaga acgcagcaaa atgcgataag 240
taatgtgaat tgcagaattc agtgaatcat cgaatctttg aacgcacatt gcgcccgcca 300
gtattctggc gggcatgcct gttcgagcgt catttcaacc ctcaagccca gcttggtgtt 360
gggactcgcg agtcaaatcg cgttccccaa attgattggc ggtcacgtcg agcttccata 420
gcgtagtagt aaaaccctcg ttactggtaa tcgtcgcggc cacgccgtta aaccccaact 480
tctgaatgtt gacctcggat caggtaggaa tacccgctga ac 522

<210> SEQ ID NO 6
<211> LENGTH: 521
<212> TYPE: DNA
<213> ORGANISM: Gibberella zeae

<400> SEQUENCE: 6
tccgttggtg aaccagcgga gggatcatta ccgagtttac aactcccaaa cccctgtgaa 60
cataccttat gttgcctcgg cggatcagcc cgcgccccgt aaaaagggac ggcccgccgc 120
aggaacccta aactctgttt ttagtggaac ttctgagtat aaaaaacaaa taaatcaaaa 180
ctttcaacaa cggatctctt ggttctggca tcgatgaaga acgcagcaaa atgcgataag 240
taatgtgaat tgcagaattc agtgaatcat cgaatctttg aacgcacatt gcgcccgcca 300
gtattctggc gggcatgcct gttcgagcgt catttcaacc ctcaagccca gcttggtgtt 360
gggagctgca gtcctgctgc actccccaaa tacattggcg gtcacgtcga gcttccatag 420
cgtagtaatt tacacatcgt tactggtaat cgtcgcggcc acgccgttaa accccaactt 480
ctgaatgttg acctcggatc aggtaggaat acccgctgaa c 521

<210> SEQ ID NO 7
<211> LENGTH: 534
<212> TYPE: DNA
<213> ORGANISM: Fusarium proliferatum

<400> SEQUENCE: 7

-continued

```
tccgttggtg aaccagcgga gggatcatta ccgagtttac aactcccaaa cccctgtgaa     60

cataccaatt gttgcctcgg cggatcagcc cgctcccggt aaaacgggac ggcccgccag    120

aggaccccta aactctgttt ctatatgtaa cttctgagta aaaccataaa taaatcaaaa    180

ctttcaacaa cggatctctt ggttctggca tcgatgaaga acgcagcaaa atgcgataag    240

taatgtgaat tgcagaattc agtgaatcat cgaatctttg aacgcacatt gcgcccgcca    300

gtattctggc gggcatgcct gttcgagcgt catttcaacc ctcaagcccc cgggtttggt    360

gttggggatc ggcgagccct tgcggcaagc cggccccgaa atctagtggc ggtctcgctg    420

cagcttccat tgcgtagtag taaaaccctc gcaactggta cgcggcgcgg ccaagccgtt    480

aaacccccaa cttctgaatg ttgacctcgg atcaggtagg aatacccgct gaac          534


<210> SEQ ID NO 8
<211> LENGTH: 522
<212> TYPE: DNA
<213> ORGANISM: Fusarium verticillioides (syn. F. moniliforme)

<400> SEQUENCE: 8

tccgttggtg aaccagcgga gggatcatta ccgagtttac aactcccaaa cccctgtgaa     60

cataccaatt gttgcctcgg cggatcagcc cgctcccggt aaaacgggac ggcccgccag    120

aggaccccta aactctgttt ctatatgtaa cttctgagta aaaccataaa taaatcaaaa    180

ctttcaacaa cggatctctt ggttctggca tcgatgaaga acgcagcaaa atgcgataag    240

taatgtgaat tgcagaattc agtgaatcat cgaatctttg aacgcacatt gcgcccgcca    300

gtattctggc gggcatgcct gttcgagcgt catttcaacc ctcaagccca gcttggtgtt    360

gggactcgcg agtcaaatcg cgttccccaa attgattggc ggtcacgtcg agcttccata    420

gcgtagtagt aaaaccctcg ttactggtaa tcgtcgcggc cacgccgtta aaccccaact    480

tctgaatgtt gacctcggat caggtaggaa tacccgctga ac                       522


<210> SEQ ID NO 9
<211> LENGTH: 19
<212> TYPE: DNA
<213> ORGANISM: Artificial sequence
<220> FEATURE:
<221> NAME/KEY: misc_feature
<222> LOCATION: (1)..(19)
<223> OTHER INFORMATION: Primer ITS1

<400> SEQUENCE: 9

tccgtaggtg aacctgcgg                                                  19


<210> SEQ ID NO 10
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer ITS2

<400> SEQUENCE: 10

gctgcgttct tcatcgatgc                                                 20


<210> SEQ ID NO 11
<211> LENGTH: 20
<212> TYPE: DNA
<213> ORGANISM: Artificial sequence
<220> FEATURE:
```

-continued

<221> NAME/KEY: misc_feature
<222> LOCATION: (1)..(20)
<223> OTHER INFORMATION: Primer ITS3

<400> SEQUENCE: 11
gcatcgatga agaacgcagc 20

<210> SEQ ID NO 12
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer ITS4

<400> SEQUENCE: 12
tcctccgctt attgatatgc 20

<210> SEQ ID NO 13
<211> LENGTH: 21
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer FCORN1

<400> SEQUENCE: 13
gcaacttgga gaagtggcaa g 21

<210> SEQ ID NO 14
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer FCORN2

<400> SEQUENCE: 14
aagtcttcca gtatggggag 20

<210> SEQ ID NO 15
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer FSUB1

<400> SEQUENCE: 15
gtccgatatc tttaggaggc 20

<210> SEQ ID NO 16
<211> LENGTH: 21
<212> TYPE: DNA
<213> ORGANISM: Artificial sequence
<220> FEATURE:
<221> NAME/KEY: misc_feature
<222> LOCATION: (1)..(21)
<223> OTHER INFORMATION: Primer FSUB2

<400> SEQUENCE: 16
tcaactagac taccaactca g 21

-continued

<210> SEQ ID NO 17
<211> LENGTH: 21
<212> TYPE: DNA
<213> ORGANISM: Artificial sequence
<220> FEATURE:
<221> NAME/KEY: misc_feature
<222> LOCATION: (1)..(21)
<223> OTHER INFORMATION: Primer FSUB3

<400> SEQUENCE: 17
caaatctaag gctggcttgt a 21

<210> SEQ ID NO 18
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer FVERT1

<400> SEQUENCE: 18
tggtggacta gtctgaatcc 20

<210> SEQ ID NO 19
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: Primer FVERT2

<400> SEQUENCE: 19
tcaactacga ctaacccacc 20

<210> SEQ ID NO 20
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Primer FPRO1

<400> SEQUENCE: 20
taaactaact caactagacg ag 22

<210> SEQ ID NO 21
<211> LENGTH: 19
<212> TYPE: DNA
<213> ORGANISM: Artificial sequence
<220> FEATURE:
<221> NAME/KEY: misc_feature
<222> LOCATION: (1)..(19)
<223> OTHER INFORMATION: Primer FPRO2

<400> SEQUENCE: 21
gatttcgggg ccggcttgc 19

<210> SEQ ID NO 22
<211> LENGTH: 18
<212> TYPE: DNA
<213> ORGANISM: Artificial sequence
<220> FEATURE:
<221> NAME/KEY: misc_feature
<222> LOCATION: (1)..(18)
<223> OTHER INFORMATION: Primer FPRO3

-continued

```
<400> SEQUENCE: 22

cgcaagggct cgccgatc                                              18


<210> SEQ ID NO 23
<211> LENGTH: 25
<212> TYPE: DNA
<213> ORGANISM: Artificial sequence
<220> FEATURE:
<221> NAME/KEY: misc_feature
<222> LOCATION: (1)..(25)
<223> OTHER INFORMATION: Primer MS1

<400> SEQUENCE: 23

cagcagtcaa gaatattagt caatg                                      25


<210> SEQ ID NO 24
<211> LENGTH: 22
<212> TYPE: DNA
<213> ORGANISM: Artificial sequence
<220> FEATURE:
<221> NAME/KEY: misc_feature
<222> LOCATION: (1)..(22)
<223> OTHER INFORMATION: Primer MS2

<400> SEQUENCE: 24

gcggattatc gaattaaata ac                                         22
```